US009880067B2

(12) United States Patent
Isailovic

(10) Patent No.: US 9,880,067 B2
(45) Date of Patent: Jan. 30, 2018

(54) MECHANICAL AGITATOR WITH SEAL HOUSING ASSEMBLY

(71) Applicant: Pall Corporation, Port Washington, NY (US)

(72) Inventor: Bojan Isailovic, Portsmouth (GB)

(73) Assignee: Pall Corporation, Port Washington, NY (US)

( * ) Notice: Subject to any disclaimer, the term of this patent is extended or adjusted under 35 U.S.C. 154(b) by 716 days.

(21) Appl. No.: 14/094,925

(22) Filed: Dec. 3, 2013

(65) Prior Publication Data

US 2015/0151261 A1   Jun. 4, 2015

(51) Int. Cl.
| *F16M 11/04* | (2006.01) |
| *G01M 3/28* | (2006.01) |
| *F16M 11/42* | (2006.01) |
| *B01F 7/22* | (2006.01) |
| *B01F 7/00* | (2006.01) |
| *B01F 15/00* | (2006.01) |
| *B01F 7/16* | (2006.01) |
| *C12M 1/06* | (2006.01) |
| *F16C 35/04* | (2006.01) |

(52) U.S. Cl.
CPC ....... *G01M 3/2853* (2013.01); *B01F 7/00725* (2013.01); *B01F 7/162* (2013.01); *B01F 7/1695* (2013.01); *B01F 7/22* (2013.01); *B01F 15/0085* (2013.01); *B01F 15/00668* (2013.01); *C12M 27/02* (2013.01); *F16M 11/04* (2013.01); *F16M 11/42* (2013.01); *B01F 2015/0011* (2013.01); *B01F 2015/00084* (2013.01); *F16C 35/045* (2013.01)

(58) Field of Classification Search
CPC .......... B01F 15/00668; B01F 15/00675; B01F 15/00681; C12M 27/02; F16J 15/3276; F16J 15/348
USPC .......................... 366/331; 277/637, 640, 907
See application file for complete search history.

(56) References Cited

U.S. PATENT DOCUMENTS

| 2,096,597 A | * | 10/1937 | Seabrooks | ................ B01F 7/06 366/331 |
| 2,911,240 A | * | 11/1959 | Boutros | ................... F16J 15/54 277/370 |
| 3,767,169 A | | 10/1973 | Carpigiani | |
| 4,189,157 A | | 2/1980 | Mahan et al. | |
| 4,577,975 A | | 3/1986 | McCrory et al. | |
| 5,251,979 A | | 10/1993 | Larsen | |
| 5,584,577 A | | 12/1996 | Thies | |
| 6,391,238 B1 | | 5/2002 | Sato et al. | |

(Continued)

FOREIGN PATENT DOCUMENTS

| DE | 10 2006 001 623 A1 | 7/2007 |
| DE | 10 2010 033083 A1 | 12/2011 |

(Continued)

*Primary Examiner* — Tony G Soohoo
*Assistant Examiner* — Elizabeth Insler
(74) *Attorney, Agent, or Firm* — Leydig Voit & Mayer

(57) ABSTRACT

A mechanically driven agitator for use in bioprocessing, including a seal housing providing an integral seal around the agitator shaft is provided. Additionally, a fluid mixing assembly comprising a container and the agitator, as well as a support assembly for supporting the fluid mixing assembly, the support assembly further comprising a mounting assembly for lockably engaging the seal housing, are also provided.

17 Claims, 14 Drawing Sheets

(56) References Cited

U.S. PATENT DOCUMENTS

| | | |
|---|---|---|
| 6,708,985 B1 | 3/2004 | Doyle |
| 6,935,771 B2 | 8/2005 | Engel |
| 7,090,223 B2 | 8/2006 | Reinhard |
| 7,237,778 B1 * | 7/2007 | Althouse, III ......... F16J 15/008 277/370 |
| 7,523,644 B2 | 4/2009 | Van Winkle |
| 7,765,853 B2 | 8/2010 | Safai et al. |
| 8,096,169 B2 | 1/2012 | Bearden et al. |
| 8,505,924 B2 | 8/2013 | Dietle et al. |
| 2006/0280028 A1 | 12/2006 | West et al. |
| 2007/0159920 A1 | 7/2007 | Baumfalk et al. |
| 2009/0130757 A1 | 5/2009 | Terentiev |
| 2011/0003374 A1 | 1/2011 | Van Den et al. |
| 2011/0013473 A1 | 1/2011 | Ludwig et al. |
| 2011/0013474 A1 * | 1/2011 | Ludwig ............... B01F 3/04269 366/102 |
| 2011/0058447 A1 | 3/2011 | Reif et al. |
| 2012/0218855 A1 | 8/2012 | Kunas et al. |

FOREIGN PATENT DOCUMENTS

| | | |
|---|---|---|
| KR | 10-2008-0074896 A | 8/2008 |
| WO | WO 03/074163 A1 | 9/2003 |
| WO | WO 2007/080369 A1 | 7/2007 |
| WO | WO 2009/116002 A1 | 9/2009 |
| WO | WO 2011/071521 A1 | 6/2011 |
| WO | WO 2012/075522 A1 | 6/2012 |
| WO | WO 2013/151733 A1 | 10/2013 |

* cited by examiner

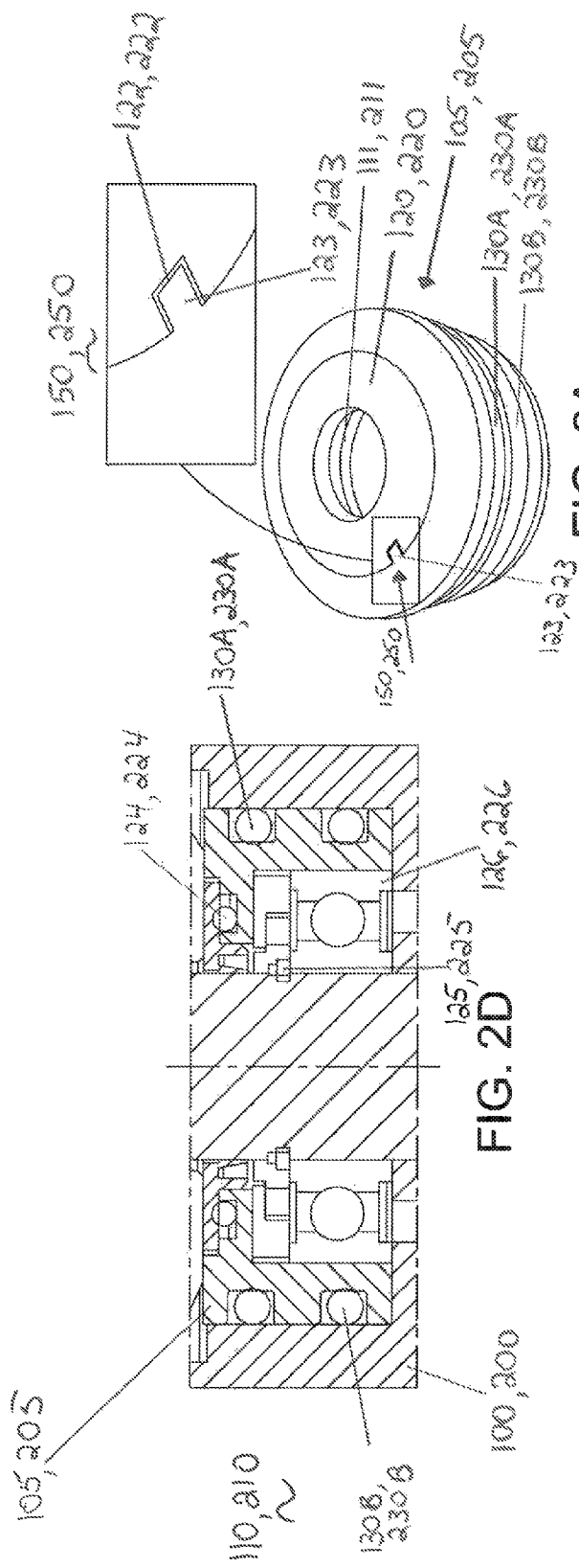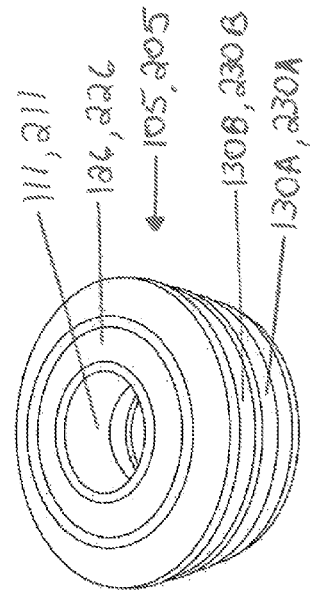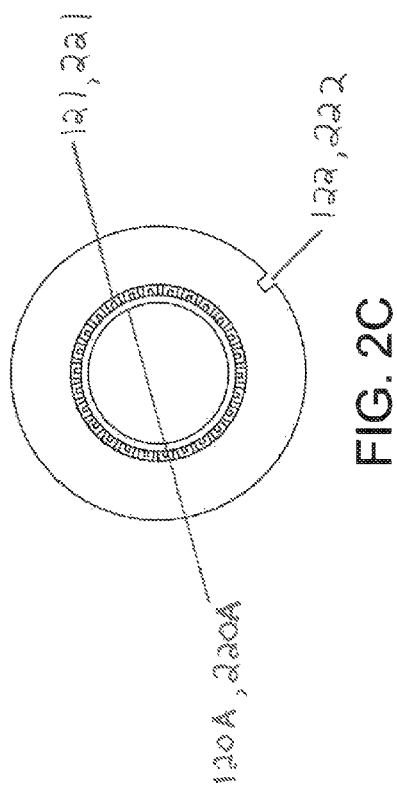

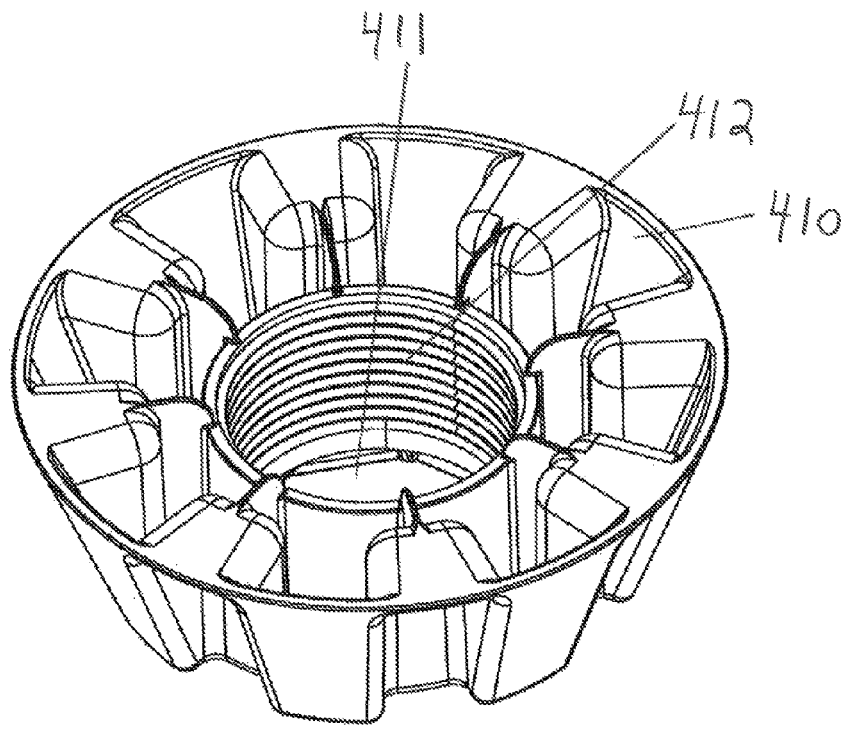
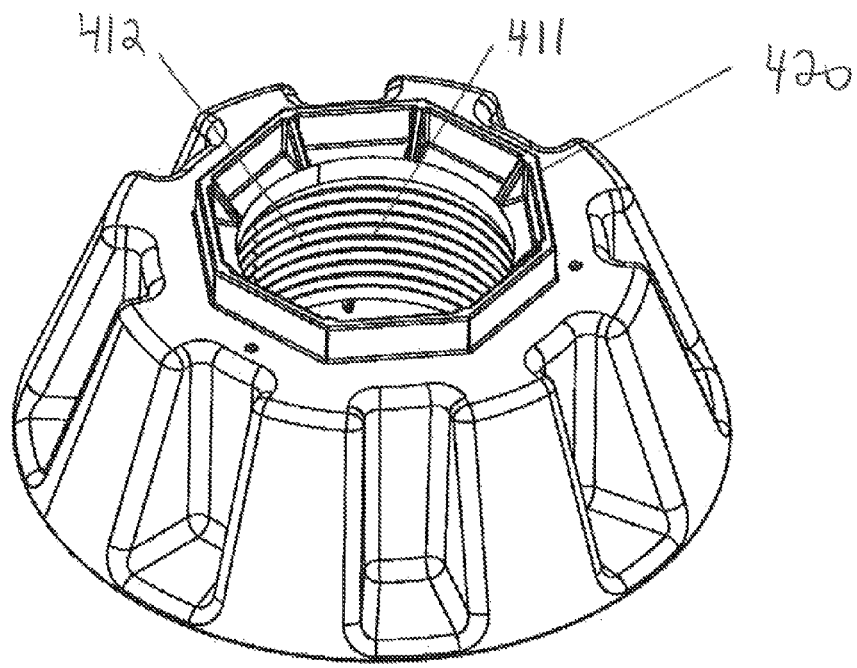

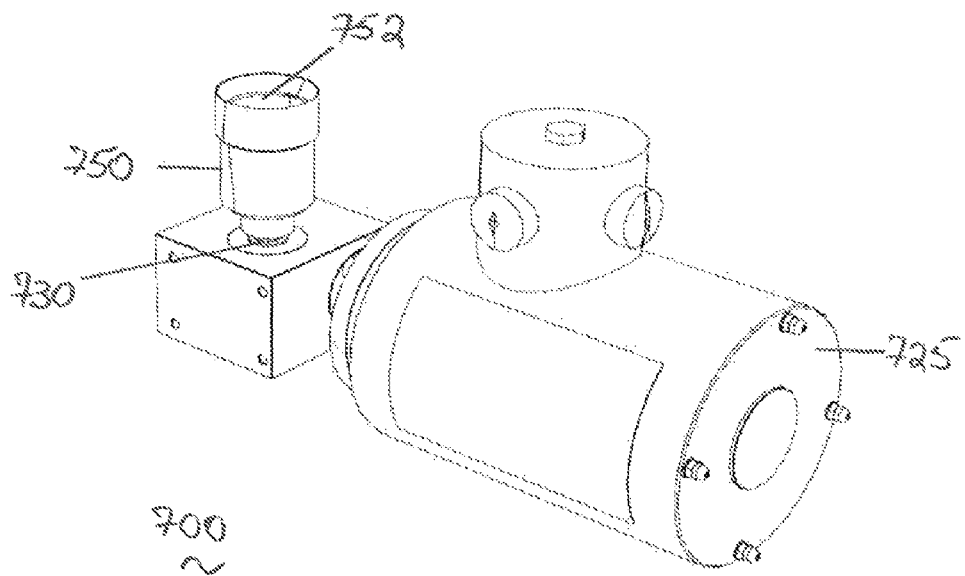
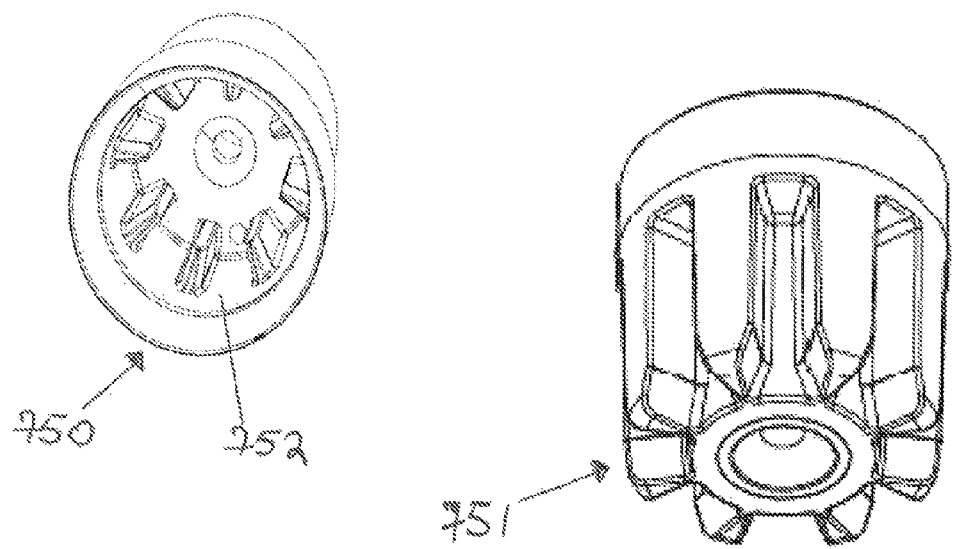
Figure 7

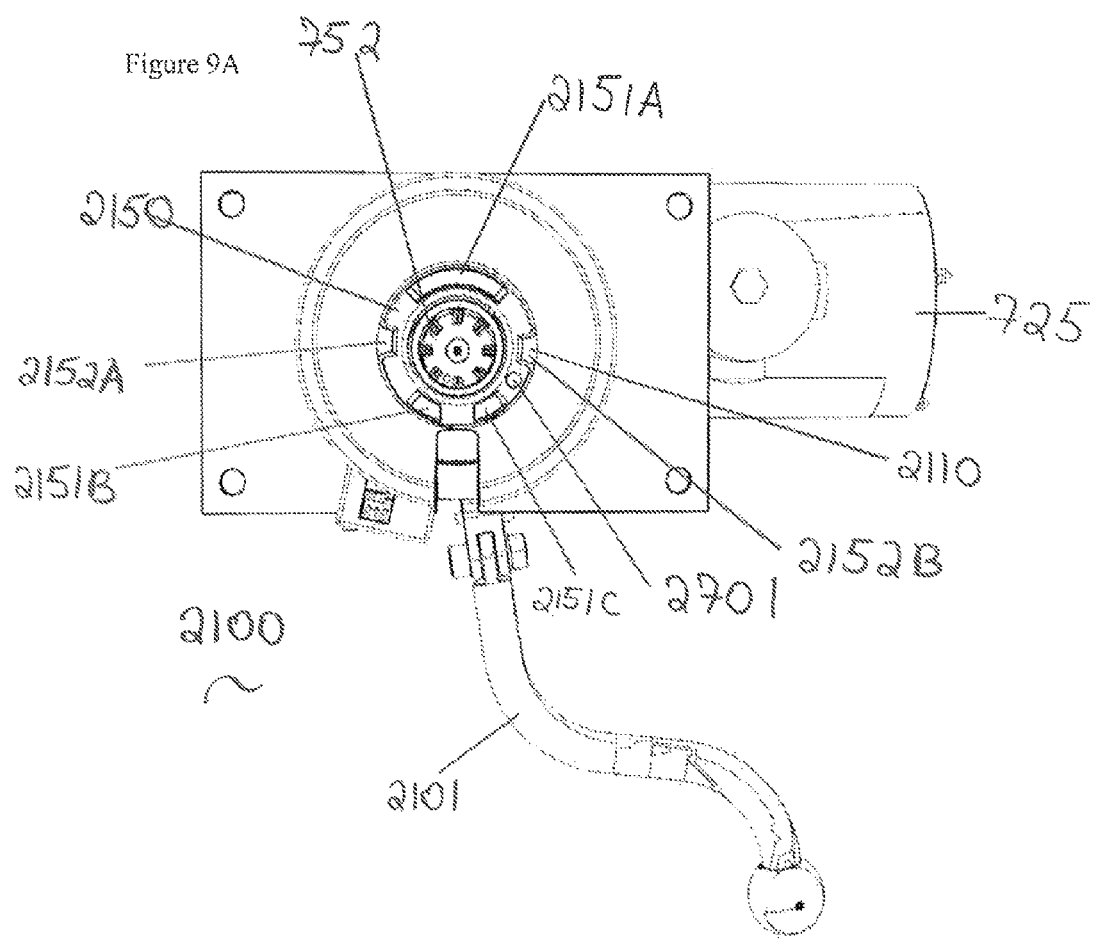

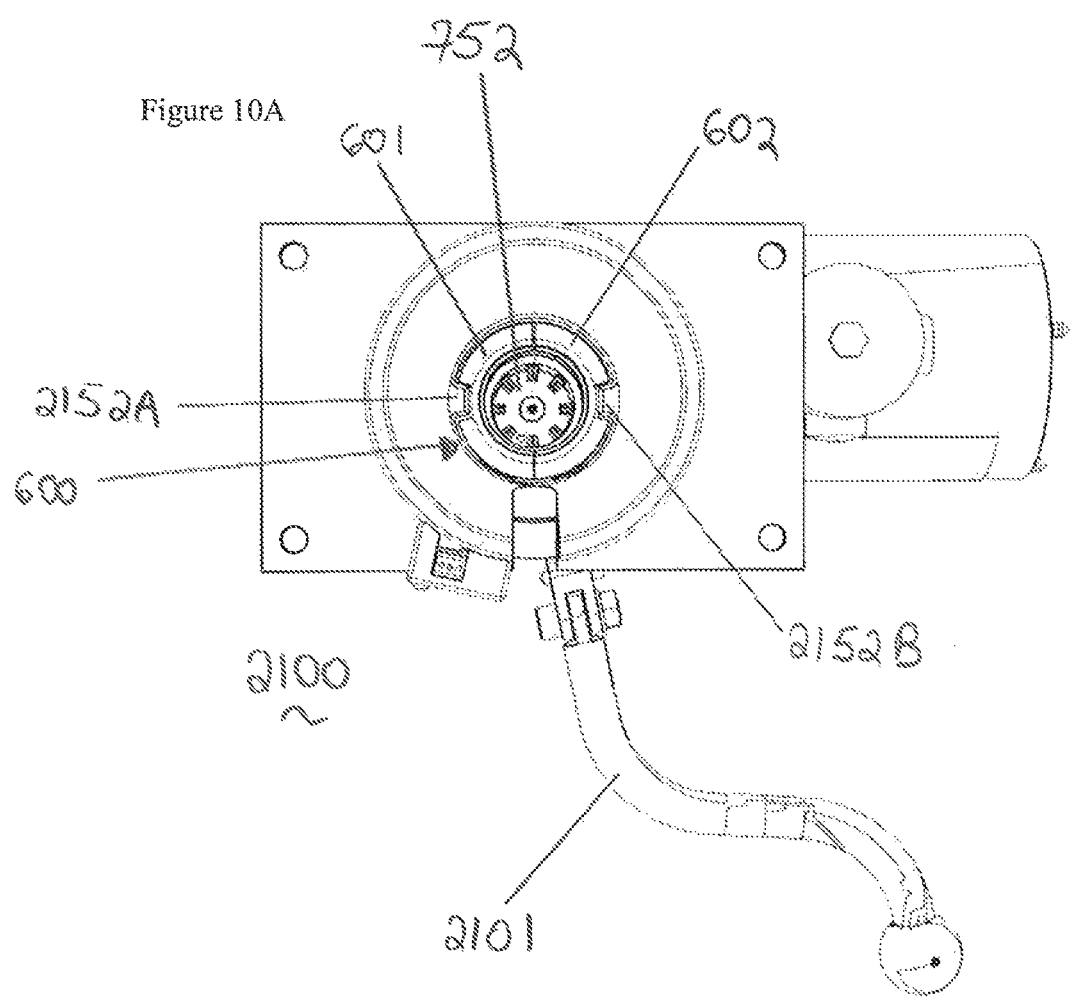

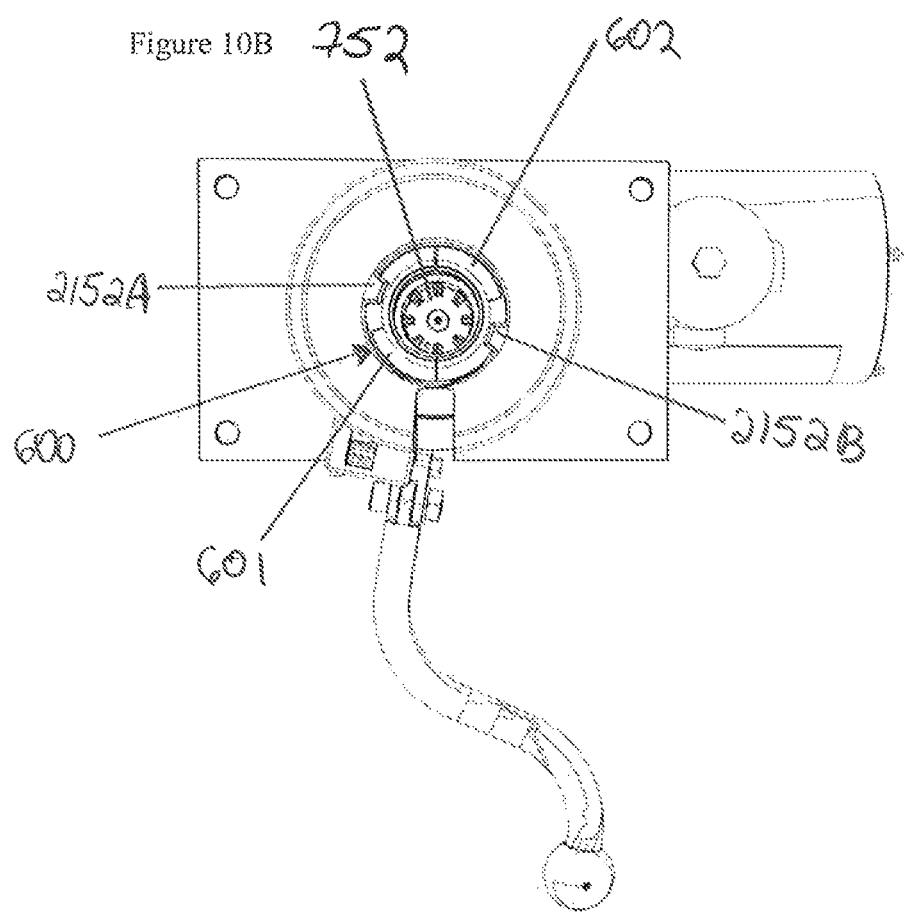

US 9,880,067 B2

MECHANICAL AGITATOR WITH SEAL HOUSING ASSEMBLY

BACKGROUND OF THE INVENTION

The preparation of fluids, particularly solutions and suspensions in the pharmaceutical and biopharmaceutical industries, typically involves thorough mixing to provide the desired distribution of ingredients in the product. Some mixing operations involve "single-use" mixers or biocontainers, and many such devices or systems include magnetically driven agitators. Magnetic mixing technology is commonly promoted over mechanically driven mixing technology for single-use mixers or biocontainers in view of a perception that the seals on the rotating shaft of mechanically driven mixers fail, compromising the integrity of the mixer or the biocontainer and the fluid processed therein.

There is a need for improved sealing of mechanically driven agitators in mixers and biocontainers, particularly single-use mixers and single-use biocontainers.

The present invention provides for ameliorating at least some of the disadvantages of the prior art. These and other advantages of the present invention will be apparent from the description as set forth below.

BRIEF SUMMARY OF THE INVENTION

An embodiment of the invention provides a mechanically driven agitator for use in bioprocessing comprising (a) a rotatable shaft comprising a cylindrical element having a first end and a second end, the shaft having a vertical rotational axis; an impeller comprising a hub mounted on the first end of the rotatable shaft, the hub having a horizontal axis perpendicular to the vertical rotational axis of the shaft, and at least two arms extending from the hub; (c) a seal housing assembly comprising an upper housing portion, and a lower housing portion; wherein the upper housing portion comprises an upper seal assembly, the upper seal assembly comprising an upper shaft seal and an upper shaft bearing, the shaft seal and the shaft bearing each including an annular opening for receiving the rotatable shaft, wherein the shaft bearing is fit onto the shaft; and, wherein the lower housing portion comprises a lower seal assembly, the seal assembly comprising lower shaft seal and a lower shaft bearing, the shaft seal and the shaft bearing each including an annular opening for receiving the rotatable shaft, wherein the shaft bearing is fit onto the shaft, and the second end of the shaft passes through the lower housing portion; the lower housing portion comprising an external surface including threads; (d) a locking ring, wherein the locking ring comprises an upper face and a lower face and an opening passing through the upper face and the lower face, the opening having a surface including threads, wherein the locking ring is threadably engageable with the lower housing portion of the seal housing assembly, and the upper face of the locking ring is suitable for contacting an outer surface of a wall of a bioprocessing container; (e) a support flange sealably coupled to the upper housing portion of the seal housing assembly, the support flange including an annular opening for receiving the rotatable shaft, the flange having a lower face suitable for sealing against an inner surface of the wall of a bioprocessing container; wherein the lower face of the flange seals against the inner surface of the wall of the bioprocessing container and the upper face of the locking ring contacts the outer surface of the wall of the bioprocessing container when the internal surface of the locking ring is threadably engaged with the external surface of the lower housing portion of the seal housing assembly.

In a preferred embodiment, the upper and lower seal assembly each further comprise an anti-rotation device, the seal assemblies each further comprising a carrier housing comprising a carrier housing protrusion, the anti-rotation device comprising a notch in the seal, and the carrier housing protrusion, wherein the protrusion engages with the seal and prevents rotation of the seal.

In an embodiment, the agitator further comprises a seal integrity testing assembly, the assembly comprising an inner channel in the seal housing assembly along the rotatable shaft communicating with the upper and lower seal assemblies, wherein the lower housing portion further comprises a port communicating with the inner channel.

In other embodiments, a mixing assembly comprising an agitator, a tote for supporting the mixing assembly, a system comprising the tote, and a method for determining seal integrity of an embodiment of the mechanically driven agitator, are provided by the invention.

BRIEF DESCRIPTION OF THE SEVERAL VIEWS OF THE DRAWING(S)

FIG. 1 is a cross-sectional view of an embodiment of an agitator of the present invention, including an impeller, a rotatable shaft, a seal housing assembly comprising an upper housing portion including an upper seal assembly, and a lower housing portion including a lower seal assembly; a support flange, and a locking ring, wherein the agitator is attached to a bottom wall of a biocontainer of a mixing assembly. The Figure includes oval lines to highlight the upper and lower seal assemblies.

FIG. 2 (A-D) shows several views of a seal assembly shown in the seal housing assembly of the agitator of FIG. 1, the seal assembly comprising a carrier housing comprising a seal including a notch, and a carrier housing protrusion engaging with the notch, forming an anti-rotation feature, preventing rotation of the seal in accordance with an embodiment of the present invention. The illustrated seal assembly also comprises a bearing, and resilient rings, the rings being compressible when a carrier housing is inserted into the upper and lower housing portions of the seal housing assembly. FIG. 2A shows a top view of a seal assembly, showing the carrier housing, seal, notch, seal assembly protrusion engaging with the notch, and resilient rings. FIG. 2B shows a bottom view of the seal assembly, showing the carrier housing, bearing, and resilient rings. FIG. 2C shows a bottom view of the seal, showing a sealing lip, an energizing spring, and the notch. FIG. 2D shows a cross-sectional view of the seal assembly fitted into a housing portion of the seal housing assembly.

FIG. 3 shows the locking ring in the embodiment of the agitator shown in FIG. 1. FIG. 3A shows a top view, and FIG. 3B shows a bottom view, wherein the locking ring has an opening passing through the ring, wherein the opening has a threaded surface.

FIG. 4 is a perspective view of the agitator shown in FIG. 1 (without the impeller), wherein the view also shows an alignment device (for engagement with a mounting assembly), attached to the lower housing portion of the seal housing assembly, as well as a first coupling fitting attached to the lower end of the shaft (engageable with a second coupling fitting shown in FIG. 7), and wherein the lower housing portion further comprises a port for communicating with the channel(s) of the integrity testing assembly.

FIG. 7 shows a mechanical drive assembly, comprising a motor, a driveshaft, and a coupler device for coupling the driveshaft to the rotatable shaft of the agitator. The Figure also shows the first coupling fitting shown in FIG. 4 (illustrated as a shaft coupling) engageable with a second coupling fitting (shown as a socket coupling) provided by the coupler device.

Figure 9B:
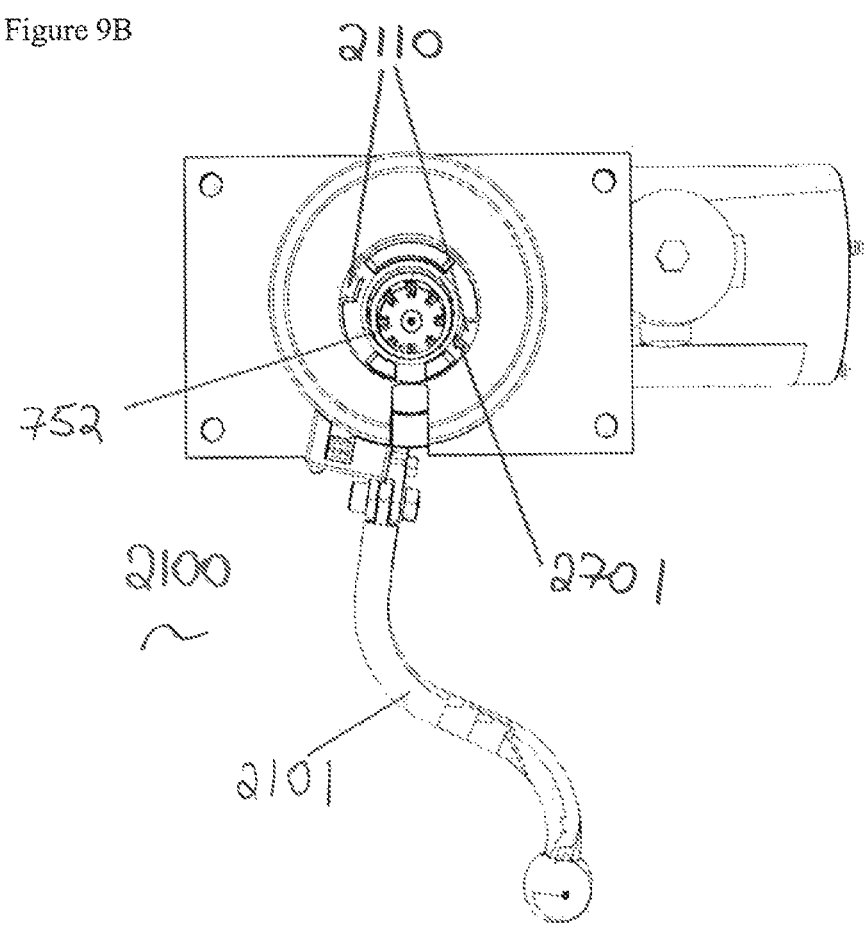

FIG. 9 (A-B) shows perspective views of an embodiment of the mounting assembly in the unlocked (FIG. 9A) and locked (FIG. 9B) positions, wherein the mounting assembly comprises a moveable seat, an engagement assembly comprising notches and protrusions for engaging with the lower housing portion of the seal housing assembly, and, an actuator for moving the moveable seat to provide a lock between the lower housing portion of the seal housing assembly and a tote after the engagement assembly engages with the lower housing portion of the seal housing assembly (FIG. 9B), and for unlocking the lower housing portion of the seal housing assembly from the tote (FIG. 9A). FIG. 9A also shows a first sensor for detecting the correct positioning of the lower housing portion of the seal housing assembly in the mounting assembly.

Figure 4:
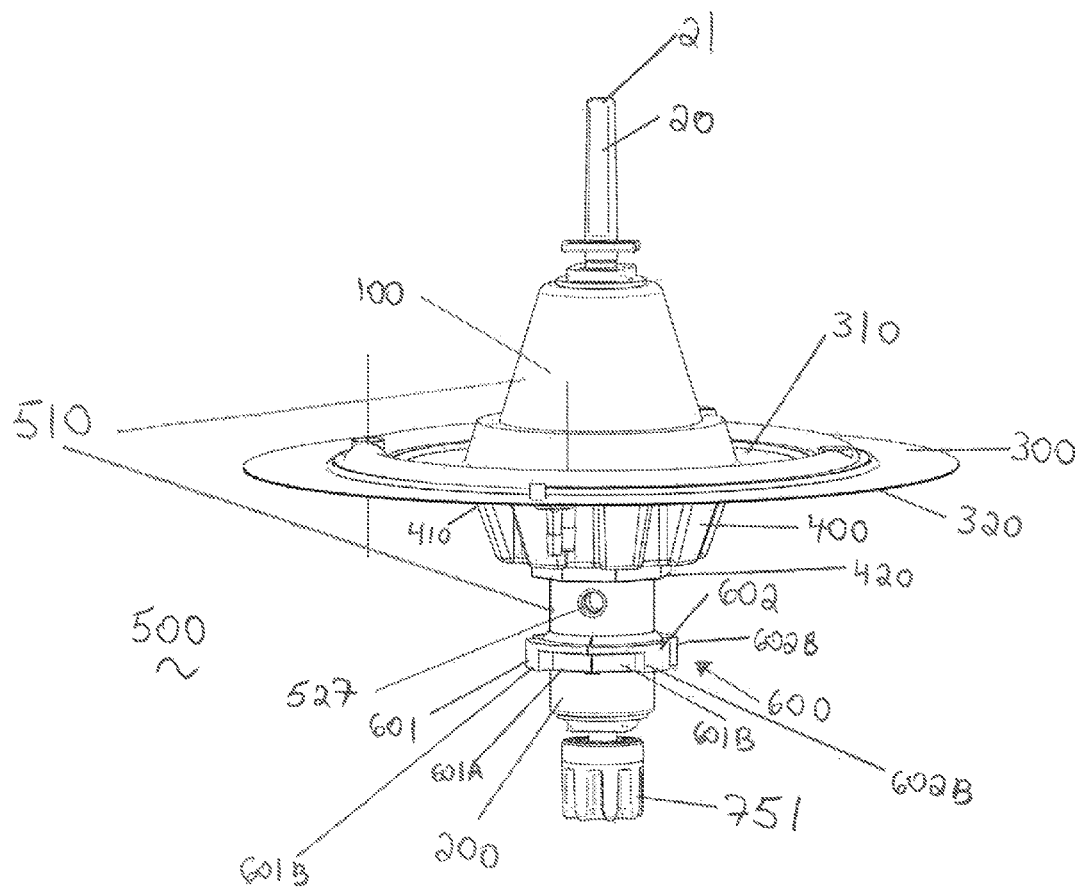

FIG. 10 (A-B) shows perspective views of the mounting assembly shown in FIG. 9, when the alignment device attached to the lower housing portion of the seal housing assembly shown in FIG. 4 is engaged with the engagement assembly (lower housing portion of the seal housing assembly not shown). FIG. 10A shows the alignment device in the correct position in the engagement assembly when the engagement assembly is in the unlocked position, and FIG. 10B shows the alignment device engaged with the engagement assembly when the engagement assembly is in the locked position.

Figure 11A:
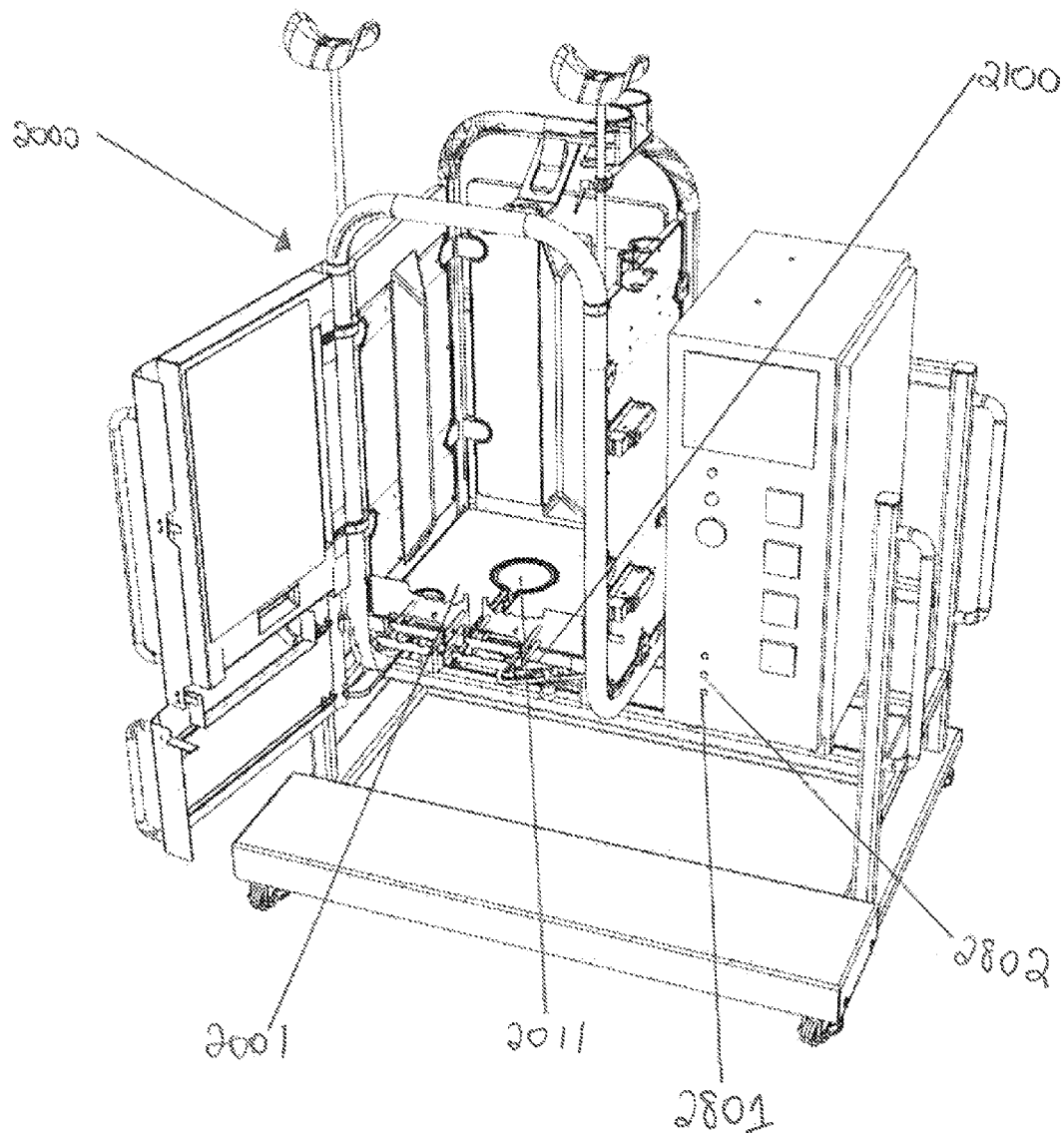
Figure 11B:
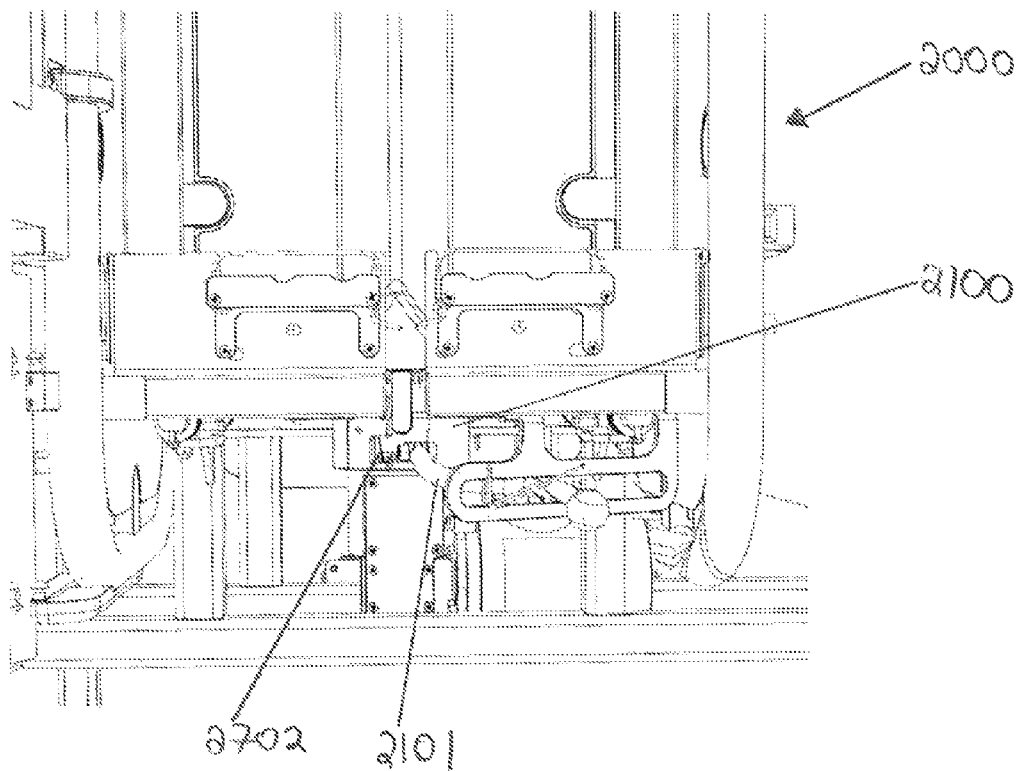
Figure 11C:
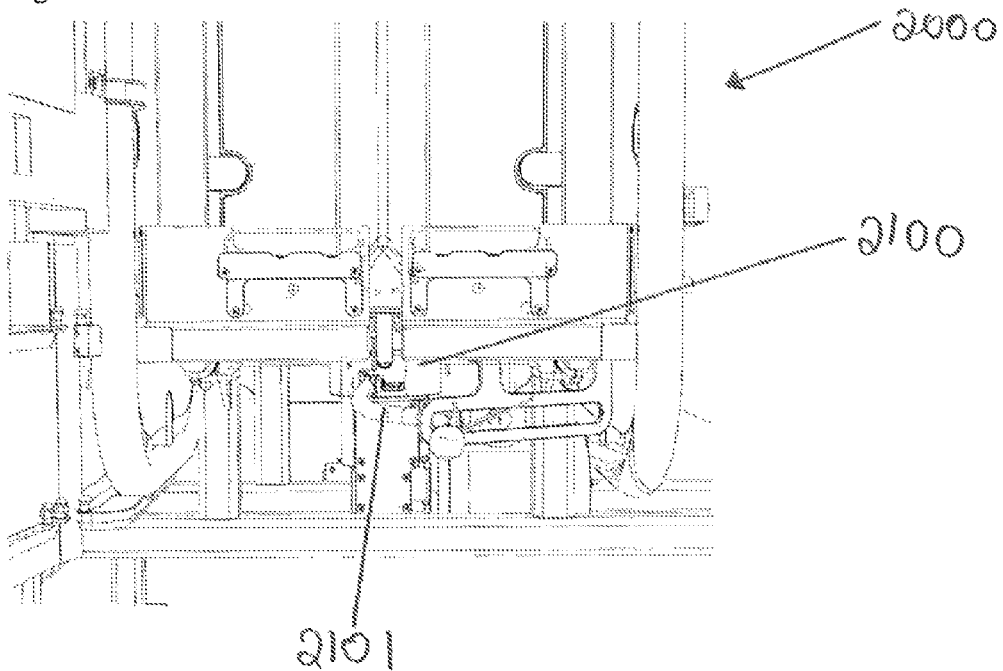

FIG. 11 (A-C) shows a tote for supporting the mixing assembly, wherein the tote has a bottom wall further comprising the mounting assembly mounted thereto, wherein the mounting assembly receives the lower housing portion of the seal housing assembly and the alignment device and can lock the seal housing assembly into correct position. FIG. 11A shows the bottom wall of the tote, as well as a control cabinet with light indicators arranged to show an operator that the seal housing assembly is in the correct position in the moveable seat, and locked into position. FIGS. 11B and 11C show the actuator of the mounting assembly in the unlocked and locked positions, respectively. FIG. 11B also shows a second sensor for detecting when the actuator has moved the moveable seat to provide the locked position.

DETAILED DESCRIPTION OF THE INVENTION

Advantageously, the integrity of a mechanical seal around a rotating shaft of a mechanical agitator used in mixers and bioreactors, especially single-use mixers and single-use bioreactors, can be ensured. Mixers and bioreactors can be easily and efficiently coupled to, and decoupled from, fixed hardware such as a tote. Without being bound to any particular theory, it is believed that the seal housing assembly can be efficiently supported and aligned in a mixing assembly including the seals, as well as in a tote receiving and supporting the mixing assembly. Alternatively, or additionally, the correct location of the seal housing assembly in the support assembly can be ensured, and the correctly located seal housing assembly can be locked in place in the tote. Moreover, the seal integrity of the seals in the agitator can be tested pre-, post- and/or during a process run to assure the user of the seal integrity, thus reducing losses of valuable fluid due to leaks or premature shutdown for fear of compromised biocontainer integrity.

Additionally, without being bound to any particular theory, it is believed that (1) the use of an anti-rotation device to prevent rotation of a seal in the seal housing assembly reduces wear in the sealing lip of the seal and/or (2) the use of a carrier housing comprising a seal and bearing provides good alignment between the seal and bearing and in turn between the seal and the rotating shaft, and thus reduces wear in the sealing lip of the seal.

In accordance with an embodiment of the present invention, a mechanically driven agitator for use in bioprocessing is provided comprising (a) a rotatable shaft comprising a cylindrical element having a first end and a second end, the shaft having a vertical rotational axis; an impeller comprising a hub mounted on the first end of the rotatable shaft, the hub having a horizontal axis perpendicular to the vertical rotational axis of the shaft, and at least two arms extending from the hub; (c) a seal housing assembly comprising an upper housing portion, and a lower housing portion; wherein the upper housing portion comprises an upper seal assembly, the upper seal assembly comprising an upper shaft seal and an upper shaft bearing, the shaft seal and the shaft bearing each including an annular opening for receiving the rotatable shaft, wherein the shaft bearing is fit onto the shaft; and, wherein the lower housing portion comprises a lower seal assembly, the seal assembly comprising lower shaft seal and a lower shaft bearing, the shaft seal and the shaft bearing each including an annular opening for receiving the rotatable shaft, wherein the shaft bearing is fit onto the shaft, and the second end of the shaft passes through the lower housing portion; the lower housing portion comprising an external surface including threads; (d) a locking ring, wherein the locking ring comprises an upper face and a lower face and an opening passing through the upper face and the lower face, the opening having a surface including threads, wherein the locking ring is threadably engageable with the lower housing portion of the seal housing assembly, and the upper face of the locking ring is suitable for contacting an outer surface of a wall of a bioprocessing container; (e) a support flange sealably coupled to the upper housing portion of the seal housing assembly, the support flange including an annular opening for receiving the rotatable shaft, the flange having a lower face suitable for sealing against an inner surface of the wall of a bioprocessing container; wherein the lower face of the flange seals against the inner surface of the wall of the bioprocessing container and the upper face of the locking ring contacts the outer surface of the wall of the bioprocessing container when the internal surface of the locking ring is threadably engaged with the external surface of the lower housing portion of the seal housing assembly.

In a preferred embodiment, the upper and lower seal assembly each further comprise an anti-rotation device, the seal assemblies each further comprising a carrier housing comprising a carrier housing protrusion, the anti-rotation device comprising a notch in the seal, and the carrier housing protrusion, wherein the protrusion engages with the seal and prevents rotation of the seal.

In an embodiment, the agitator further comprises a seal integrity testing assembly, the assembly comprising an inner channel along the rotatable shaft communicating with the upper and lower seal assemblies, wherein the lower housing portion further comprises a port communicating with the inner channel.

In some embodiments of the agitator, the upper and lower seal assembly each further comprise at least one resilient ring that compresses when the seal assembly is fitted into the respective housing portion.

In some embodiments, the upper shaft bearing is press-fit to the shaft, and/or the lower shaft bearing is interference fit to the shaft.

In another embodiment, the agitator further comprises a first coupling fitting attached to the second end of the shaft. Preferably, a coupler device comprising a second coupling fitting is engageable with the first coupling fitting.

A mixing assembly is also provided by another embodiment of the invention, the mixing assembly comprising (a) a bioprocessing container comprising a closed container having an interior volume suitable for containing fluid, the container comprising a bottom wall, a top wall, and at least one side wall, the side wall(s) being joined to the top wall and the bottom wall; and at least an inlet port, and a drain port, wherein the bioprocessing container further comprises (b) an embodiment of the mechanically driven agitator, attached to the bottom wall or the top wall.

A tote for supporting a mixing assembly according to an embodiment of the invention typically comprises a body with side faces and a floor for receiving the mixing assembly. The floor of the tote according to an embodiment of the invention includes an opening for receiving the lower housing portion of the seal housing assembly of an embodiment of the mixing assembly, the tote further comprising a support assembly comprising: (i) a moveable seat arranged in the opening in the floor; (ii) an engagement assembly comprising at least one protrusion for engaging with the lower housing portion of the seal housing assembly; and, (iii) an actuator for moving the moveable seat to provide a lock between the lower housing portion of the seal housing assembly and the tote after the engagement assembly engages with the lower housing portion of the seal housing assembly, and for unlocking the lower housing portion of the seal housing from the tote.

In an embodiment of the tote, an alignment device is attached to the lower housing portion of the seal housing assembly, and the engagement assembly engages with the alignment device.

In another embodiment of the tote, the support assembly further comprises a first sensor for detecting when the engagement assembly engages with the lower housing portion of the seal housing assembly. In a preferred embodiment, the tote further comprises a second sensor for detecting when the actuator has moved the moveable seat to provide the lock.

An embodiment of a system is also provided according to the invention, the system comprising an embodiment of the tote, and further comprising at least first and second indicators receiving signals from the first and second sensors, respectively, wherein the indicators are illuminated when the signals are received.

In yet another embodiment of the invention, a method for determining seal integrity of an embodiment of the mechanically driven agitator comprising a seal housing assembly is provided, the method comprising applying pressure to the agitator through a port communicating with an inner channel of the seal housing assembly, and determining whether the pressure is maintained for a desired period of time.

Each of the components of the invention will now be described in more detail below, wherein like components have like reference numbers.

Figure 1:
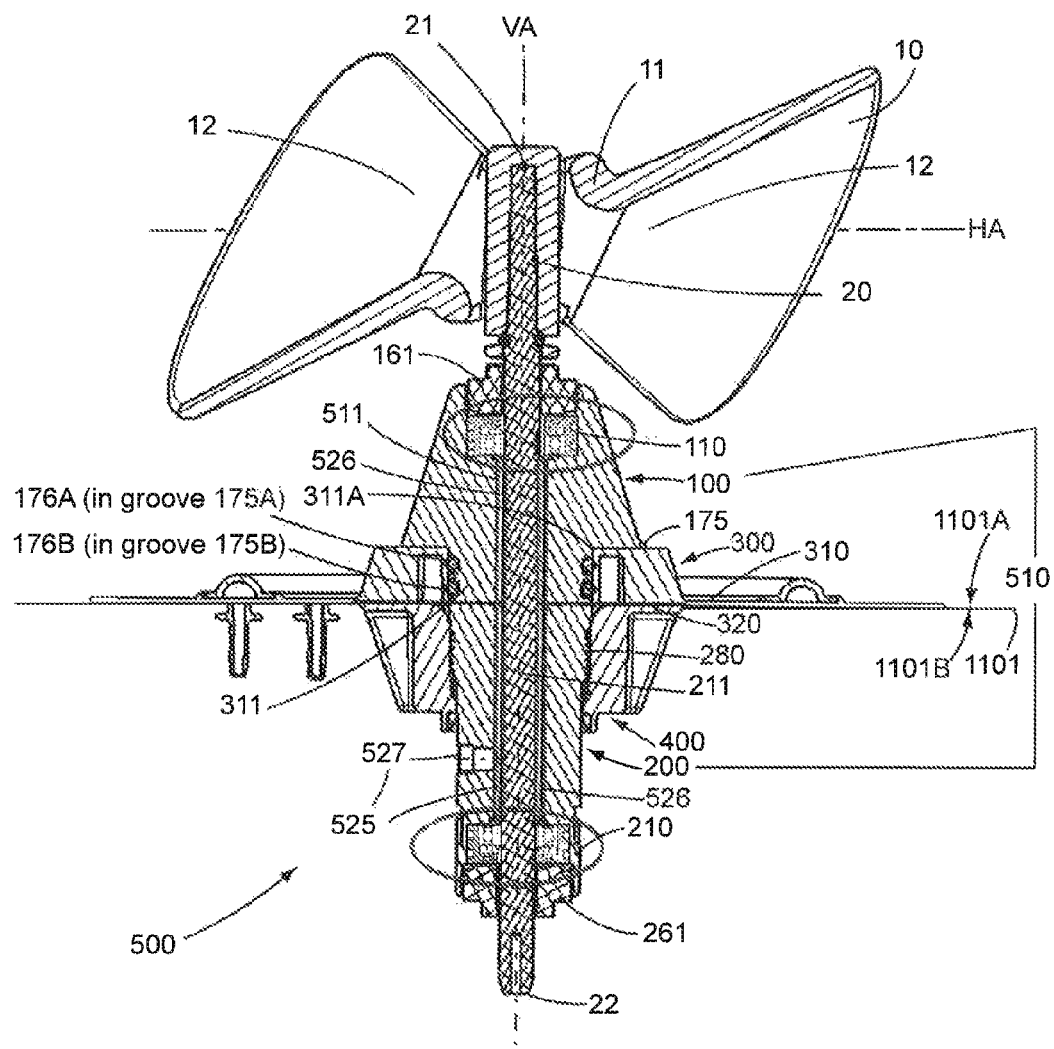

FIG. 1 illustrates, in cross-sectional view, an embodiment of a mechanically driven agitator 500 according to an embodiment of the invention, the agitator 500 comprising an impeller 10 comprising a hub 11 and at least two arms 12 extending from the hub and preferably having blades at the non-hub ends of the arms (preferably, the impeller, hub, and arms are plastic), a rotatable shaft 20 (having a vertical rotational axis VA) comprising a cylindrical element having a first end 21 and a second end 22, a seal housing assembly 510, a support flange 300 (which can comprise a sparger baseplate comprising one or more sparger ports), and a locking ring 400. The illustrated agitator has the hub mounted on the first end of the shaft, the hub having a horizontal axis HA perpendicular to the vertical rotational axis of the shaft. FIG. 1 also illustrates an impeller retaining clip engaged with the shaft and a portion of the hub.

The illustrated seal housing assembly 510 comprises an upper housing portion 100 comprising an upper portion seal assembly 110, and a lower housing portion 200 comprising a lower portion seal assembly 210, a central channel 511 passing through the seal housing assembly and the upper and lower housing portions 100, 200, and an integrity testing assembly 525 comprising an internal channel 526 communicating with the upper portion seal assembly and the lower portion seal assembly, and a port 527 communicating with the internal channel.

As shown in more detail in FIG. 2, the illustrated upper portion seal assembly 110 and lower portion seal assembly 210 each have a central channel 111, 211 respectively (for receiving the rotatable shaft) and each comprise respective seals 120, 220 with annular openings and comprising an energizing spring 121, 221, and a sealing lip 120A, 220A (e.g., a commercially available seal comprising an energizing spring and a sealing lip, such as, for example, VARISEAL (Trelleborg Sealing Solutions)), wherein the seals are preferably further modified to comprise a notch 122, 222; each portion seal assembly further comprising a resilient ring 124, 224, a circlip 125, 225, and a bearing 126, 226. Preferably, and as shown in FIG. 2 (A-D), each portion seal assembly comprises a carrier housing 105, 205 comprising the respective seal, notch, circlip, and bearing (fit onto the shaft), the respective carrier housings further comprising a carrier housing protrusion 123, 223, as well as two resilient carrier rings 130A, 130B; 230A, 230B, wherein the carrier housing protrusions 123, 223 engage with the notches 122, 222 to provide an anti-rotation device 150, 250 (preventing rotation of the seal), and the resilient carrier rings compress when fitting the carriers into the respective upper and lower housing portions of the seal housing assembly. In some embodiments, the upper and lower carrier housings are identical, for ease of production and cost effectiveness in providing the agitator.

Typically, as shown in FIG. 1, caps 161, 261 are inserted to retain the seal assemblies in the respective portions of the seal housing assemblies, and FIG. 1 illustrates the caps as threaded into the respective housing portions. The central channel 511 for receiving the rotatable shaft can have a slightly larger diameter between the upper and lower seal assemblies than along the length of the rest of the length of the central channel, to provide the internal channel 526 of the integrity testing assembly.

In some embodiments, the bearing 126 in the upper seal portion assembly is press-fit to the shaft. Alternatively, or additionally, in some embodiments, the bearing 226 in the lower seal portion assembly is interference-fit to the shaft.

Figure 6:
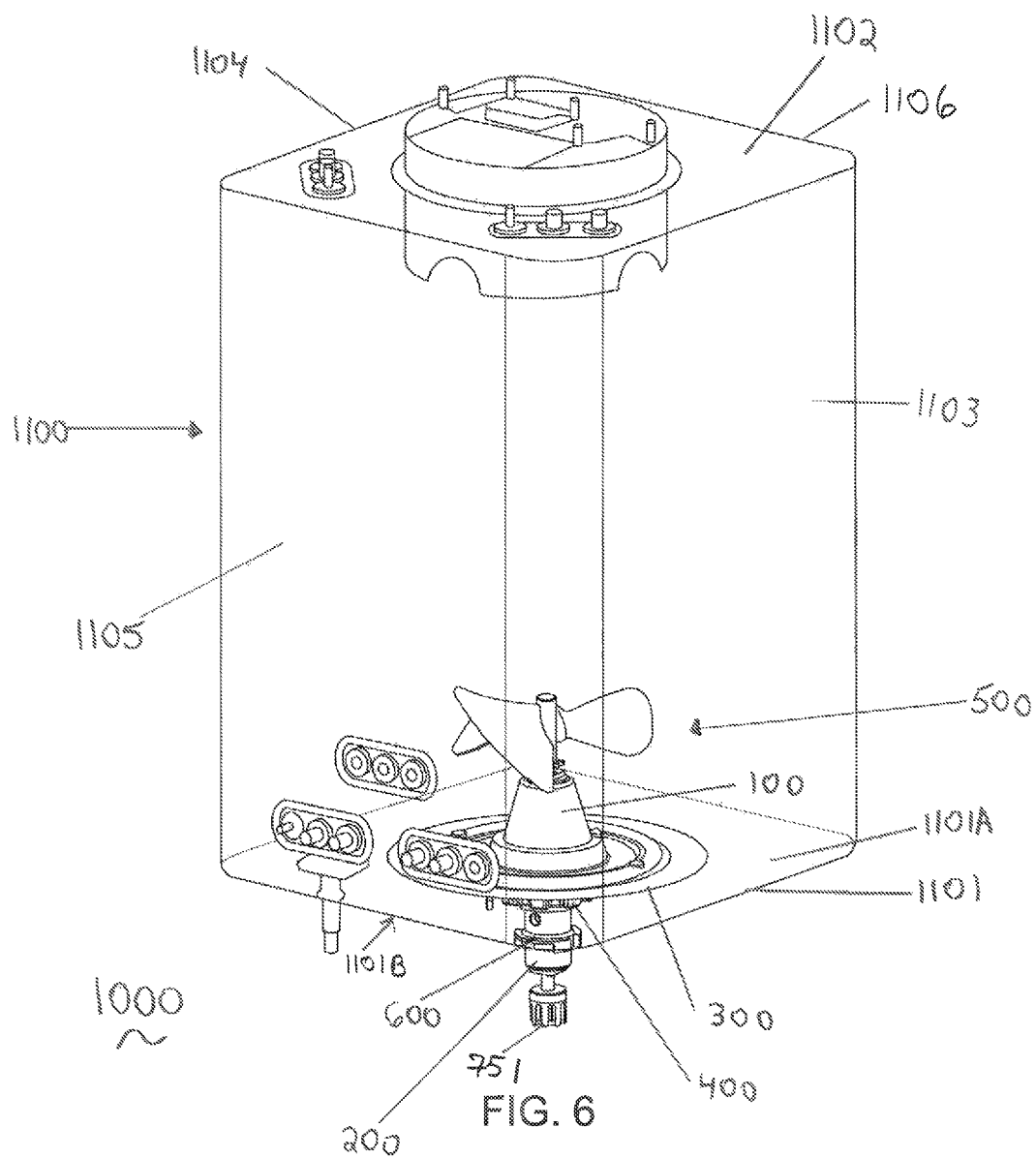
FIG. 6 is an embodiment of a mixing assembly according to an embodiment of the invention, comprising the embodiment of the agitator shown in FIG. 1, attached to the bottom wall of the biocontainer of the mixing assembly.

The agitator is mounted to a top or bottom wall of a biocontainer 1100 of mixing assembly 1000 (a bottom wall 1101 is shown in FIG. 1, a mixing assembly 1000 comprising a biocontainer 1100 is shown in FIG. 6), preferably using a support flange 300 having an upper face 310 and a lower face 320 and an opening 311 (the flange being arranged inside the mixing assembly and mounted to the upper housing portion 100 of the seal housing assembly 510) and a locking ring 400 (shown in more detail in FIG. 3) comprising an upper face 410 and a lower face 420 and an opening 411 passing through the faces, the opening including a threaded surface 412 (the locking ring being arranged outside the mixing assembly and mounted to the lower housing portion 200 of the seal assembly 510). For example, as shown in FIG. 1, the illustrated upper housing portion 100 of the seal housing assembly 510 includes a shoulder 175 and grooves 175A, 175B, and resilient rings 176A, 176B that compress and provide a seal between the wall 311A of the opening 311 of the support flange 300 and the lower part of the external surface of the upper housing portion 100 of the seal housing assembly 510, wherein the upper face 310 presses against a surface of the shoulder 175, and the lower face 320 of the flange is sealed to (preferably, welded to) an inner surface 1101A of the bottom wall 1101 of a biocontainer of a mixing assembly. In the embodiment illustrated in FIG. 1, the lower housing portion 200 of the seal housing assembly 510 has an external surface 280 comprising threads 281, and the locking ring 400 (shown in more detail in FIG. 3) is threadably engaged with the lower housing portion such that the upper face 410 of the locking ring contacts the outer surface 1101B of the bottom wall 1101 of the biocontainer of the mixing assembly (opposing the surface 1101A of the wall 1101 welded to the flange 300).

An illustrative mixing assembly 1000 comprising a closed biocontainer or closed bioprocessing container 1100 comprising a bottom wall 1101, a top wall 1102, and opposing side walls 1103, 1104, and 1105, 1106, and including a plurality of ports including at least one inlet port and a drain port, and having an interior volume suitable for containing fluid, and having the agitator 500 mounted to the bottom wall 1101 of the biocontainer 1100, is shown in FIG. 6. The biocontainer (or bioprocessing container) can have any suitable form (e.g., cylindrical (having, for example, a single continuous side wall), square, or rectangular), and in FIG. 6 is illustrated as having a generally rectangular cuboid form with a plurality of side walls.

Figure 5:
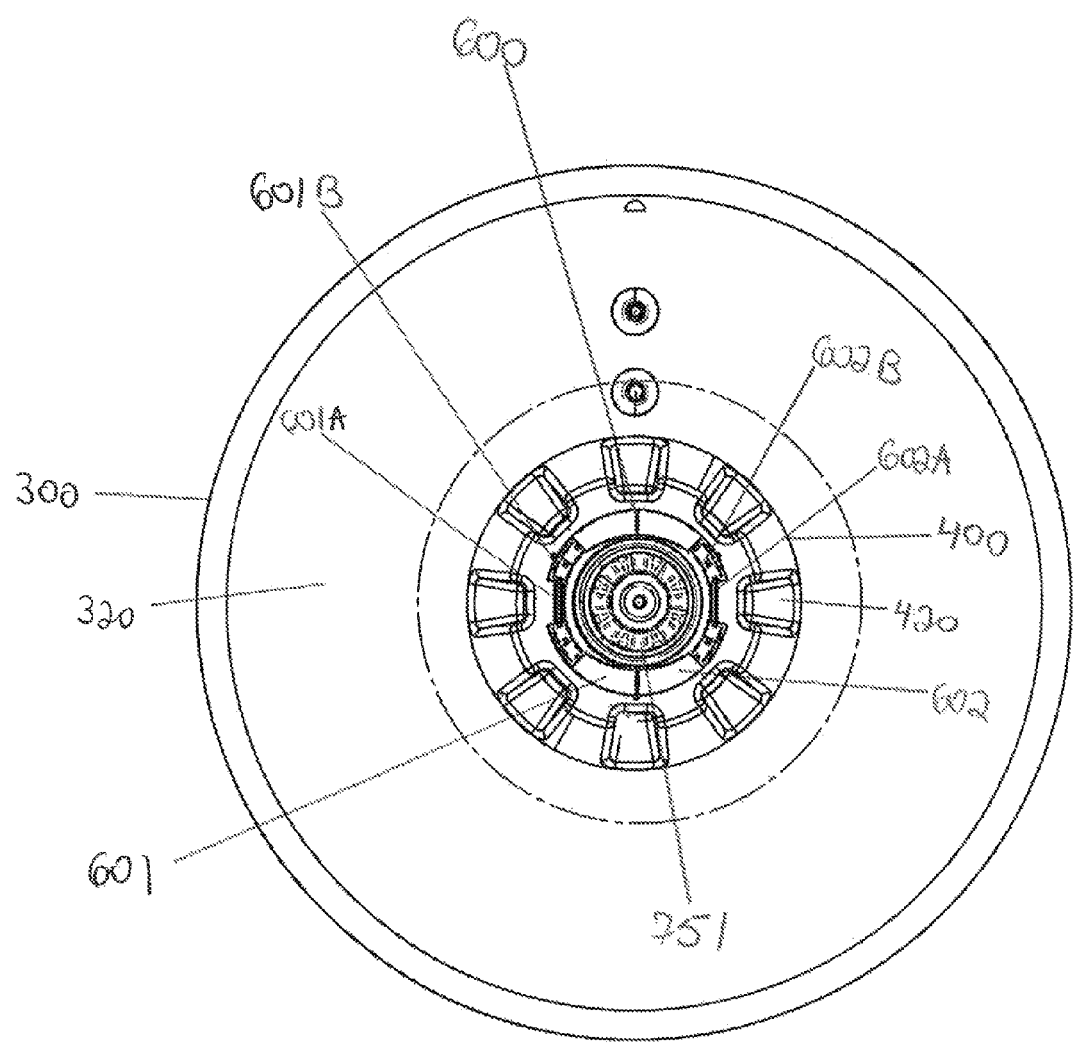
FIG. 5 is a bottom view of the agitator shown in FIG. 4.

As will be described in more detail below, an alignment device 600 is preferably mountable (more preferably, removably mountable) to the lower housing portion 200 of the seal housing assembly 510 for engagement with a mounting assembly, the mounting assembly being attached to the bottom wall of a tote. FIGS. 4 and 5 show perspective and bottom views of an agitator 500 including alignment device 600, wherein the illustrated alignment device comprises two clips 601, 602 (shown as bayonet clips), the clips comprising recesses 601A, 602A and shoulders 601B, 602B. In FIG. 5, the support flange is illustrated as a sparger baseplate including sparger ports. The embodiment of the agitator 500 shown in FIGS. 4 and 5 further comprises a first coupling fitting 751 (shown as a shaft coupling), mounted to the lower end 22 of the rotating shaft 20, for coupling to a mechanical drive assembly, such that the mechanical drive assembly can drive the agitator. FIG. 4 also shows the lower housing portion 200 of the housing assembly 510 comprising the port 527 for communicating with the internal channel 511 of the integrity testing assembly 525.

The agitator is driven by a mechanical drive assembly comprising a motor. Preferably, as shown in FIG. 7, the mechanical drive assembly 700 comprises a motor 725, an output shaft 730, and a coupler device 750. The illustrated coupler device 750, shown mounted to the output shaft 730 extending from a gearbox connected to the motor 725 (e.g., via a keyway mating with a key on a drive shaft (not shown)), comprises a second coupling fitting 752 (shown as a socket coupler) that couples to the first coupling fitting 751. The illustrated first and second coupling fittings each comprise extensions or fingers and recesses therebetween (e.g., teeth and grooves) for engagement and coupling, so that operation of the motor will cause the impeller to rotate. In some embodiments, the first coupling fitting is made from a plastic elastomeric material and the second coupling fitting is made from metal, e.g., the elastomeric material can absorb misalignment during shaft rotation, for example, to enable good alignment between the rotating shaft 20 in the seal housing assembly, and the output shaft 730.

Advantageously, embodiments of the invention comprise a mounting assembly associated with a tote (e.g., mounted to the bottom wall of the tote) to enable good alignment of the rotatable shaft in the seal housing assembly when coupled to the output shaft of the drive assembly, and prevent movement of the seal housing assembly during shaft rotation. Preferably, the mounting assembly comprises a moveable seat and an engagement assembly and at least one sensor to indicate when the lower portion of the seal housing assembly is located in the seat (as shown in FIG. 9A), more preferably, the tote (e.g., the mounting assembly) further comprises a second sensor to indicate when the seal housing assembly is locked in place (as shown in FIGS. 11B and C).

Figure 8:
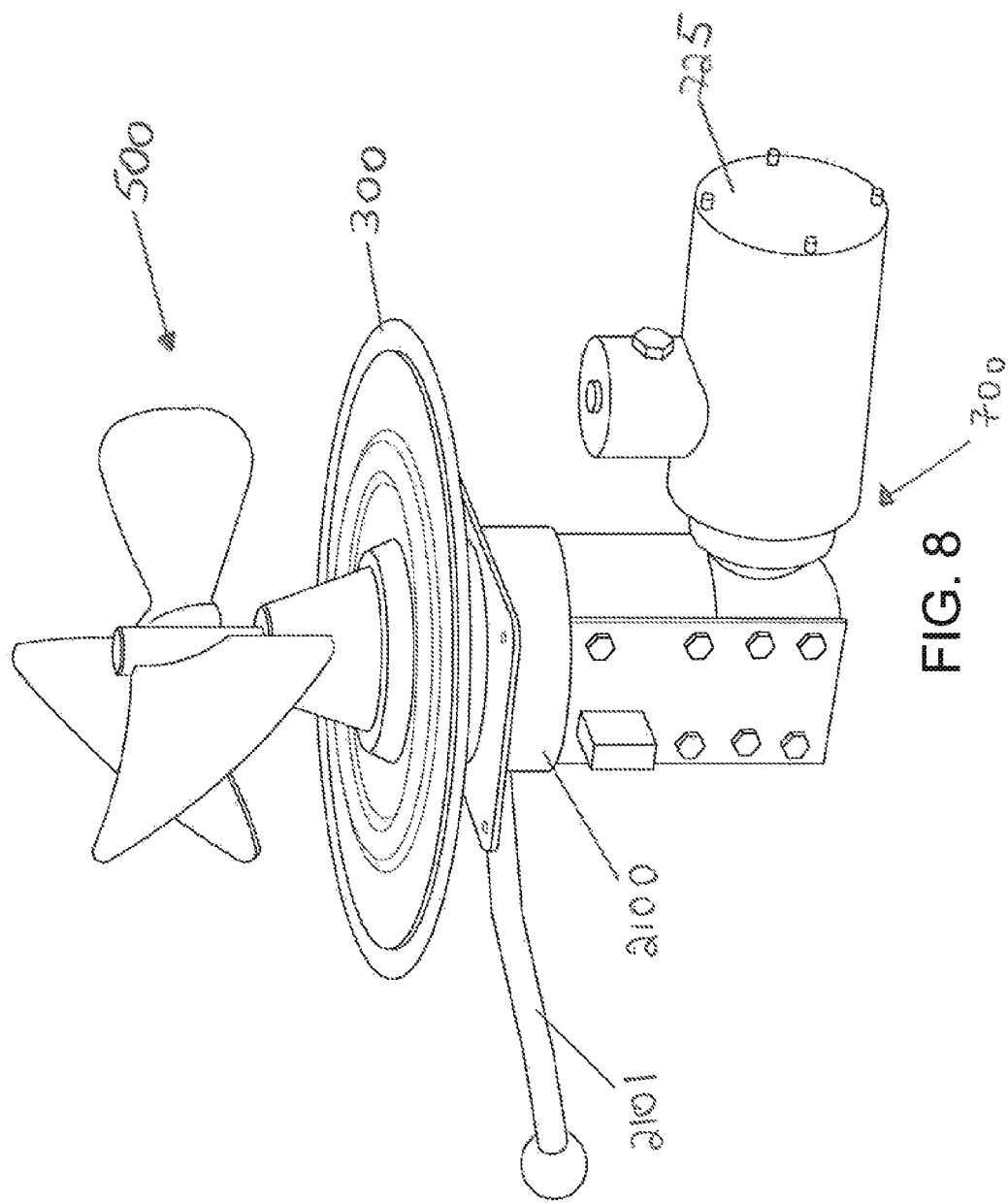
FIG. 8 shows the agitator coupled to the mechanical drive assembly, and a mounting assembly receiving the lower housing portion of the housing assembly, the mounting assembly comprising an actuator for locking and unlocking a moveable seat receiving the lower housing portion of the housing assembly.

FIG. 8 shows the agitator 500 coupled to the mechanical drive assembly 700, and a mounting assembly 2100 receiving the lower housing portion 200 of the housing assembly, the mounting assembly comprising an actuator 2101 for locking and unlocking a moveable seat 2110 (not shown, see FIG. 9) receiving the lower housing portion of the housing assembly.

FIG. 9 shows perspective views of an embodiment of the mounting assembly 2100 in the unlocked (FIG. 9A) and locked (FIG. 9B) positions, wherein the mounting assembly comprises the moveable seat 2110, an engagement assembly 2150 for engaging with the lower housing portion of the seal housing assembly (the engagement assembly comprising at least one protrusion and/or at least one stop), and, the actuator 2101 for moving the moveable seat 2110 to provide a lock between the lower housing portion of the seal housing assembly and a tote (the tote is shown in FIG. 11A) after the engagement assembly engages with the lower housing portion of the seal housing assembly (FIG. 9B), and for unlocking the lower housing portion of the seal housing assembly from the tote (FIG. 9A). FIG. 9A also shows a first sensor 2701 for detecting engagement of the lower housing portion of the seal housing assembly with the mounting assembly. In this illustrated embodiment, the engagement assembly 2150 comprises fixed curved protrusions 2151A, 2151B, 2151C for receiving the recesses 601A, 602A formed in the clips 601, 602 of the alignment device 600 (shown in FIG. 4), and moveable stops 2152A, 2152B for locking against the shoulders 601B, 602B of the clips of the alignment device.

FIG. 10 shows perspective views of the mounting assembly 2100 shown in FIG. 9, when the alignment device 600 attached to the lower housing portion 200 of the seal housing assembly shown in FIG. 4 is engaged with the engagement assembly 2150 (lower housing portion of seal housing assembly not shown). FIG. 10A shows the clips 601, 602 of the alignment device 600 engaged with the engagement assembly 2150 when the engagement assembly is in the unlocked position, and FIG. 10B shows the alignment device 600 engaged with the engagement assembly 2150 when the engagement assembly is in the locked position.

Embodiments of the invention can be used with a variety of totes that can have any suitable form, e.g., generally box-shaped or generally cylindrical bodies.

FIG. 11 shows a tote 2000 for supporting the mixing assembly, wherein the tote comprises a body with side faces and has a floor or bottom wall 2001 with an opening 2011, the bottom wall further comprising the mounting assembly 2100 mounted thereto, wherein the mounting assembly receives the lower housing portion of the seal housing assembly and the alignment device and can lock the seal housing assembly into correct position. FIG. 11A shows the bottom wall 2001 of the tote, and FIGS. 11B and 11C show the actuator 2101 of the mounting assembly in the unlocked and locked positions, respectively. FIG. 11B also shows a second sensor 2702 for detecting when the actuator has moved the moveable seat to provide the locked position. FIG. 11A also shows an embodiment of a system comprising the tote and a control cabinet with light indicators 2801 (receiving the signal from sensor 2701), and 2802 (receiving the signal from sensor 2702) arranged to show an operator that the seal housing assembly is locked into the correct position.

A variety of fluids can be processed and/or prepared (including mixing) in accordance with embodiments of the invention. Applications include, for example, cell culture (e.g., including batch and fed-batch operations of suspension and adherent cell lines), preparing sterile fluids for the pharmaceutical and/or biopharmaceutical industries, including drugs, vaccines, and intravenous fluids, antibody- and/or protein-containing fluids, and/or fluids for the food and beverage industry. Fluids mixed according to embodiments of the invention can also used, for example, as media and/or chromatography buffers.

An embodiment of a method for testing seal integrity of a mechanically driven agitator according to an embodiment of the invention comprises applying pressure to the port 527 communicating with the internal channel 526 (shown in FIGS. 1 and 4), and the pressure is analyzed over a period of time to see if the pressure is maintained, thus showing the integrity of the seals is maintained. If the pressure has decayed, the integrity of one of the seals has been breached. Illustratively, an impeller can be pressurized at about 0.6 barg for 6 minutes, and the pressure decay analyzed.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mechanically driven agitator for use in bioprocessing comprising
   (a) a rotatable shaft comprising a cylindrical element having a first end and a second end, the shaft having a vertical rotational axis;
   (b) an impeller comprising a hub mounted on the first end of the rotatable shaft, the hub having a horizontal axis perpendicular to the vertical rotational axis of the shaft, and at least two arms extending from the hub;
   (c) a seal housing assembly comprising an upper housing portion, and a lower housing portion;
   wherein the upper housing portion comprises a shoulder having a shoulder surface and a lower part having an external surface, an upper seal assembly, the upper seal assembly comprising an upper shaft seal and an upper shaft bearing, the upper shaft seal including an upper seal annular opening and the upper shaft bearing including an upper bearing annular opening for receiving the rotatable shaft, wherein the upper shaft bearing is fit onto the shaft; and,
   wherein the lower housing portion comprises a lower seal assembly, the seal assembly comprising lower shaft seal and a lower shaft bearing, the lower shaft seal including a lower seal annular opening and the lower shaft bearing including a lower bearing annular opening for receiving the rotatable shaft, wherein the lower shaft bearing is fit onto the shaft, and the second end of the shaft passes through the lower housing portion; the lower housing portion comprising an external surface including threads,
   an upper carrier housing located in the upper housing portion, a lower carrier housing located in the lower housing portion, the upper carrier housing comprising the upper shaft seal and the upper shaft bearing, the lower carrier housing comprising the lower shaft seal and the lower shaft bearing, wherein the upper seal assembly and the lower seal assembly each further comprise an anti rotation device, each of the upper and lower carrier housings comprising a carrier housing protrusion formed into each of the upper and lower carrier housings, the anti rotation device comprising a notch in the shaft seal, and the carrier housing protrusion, wherein the protrusion engages with the shaft seal and prevents rotation of the shaft seal;

(d) a locking ring, wherein the locking ring comprises an upper locking ring face and a lower locking ring face and an opening passing through the upper locking ring face and the lower locking ring face, the opening having a surface including threads, wherein the locking ring is threadably engageable with the lower housing portion of the seal housing assembly, and the upper face is suitable for contacting an outer surface of a wall of a bioprocessing container;

(e) a support flange including a flange annular opening for receiving the rotatable shaft, the flange having a flange upper face, and a flange lower face suitable for sealing against an inner surface of the wall of a bioprocessing container; wherein the flange annular opening includes a wall sealably coupled to the external surface of the lower part of the upper housing portion of the seal housing assembly;

wherein the upper face of the flange presses against the surface of the shoulder of the upper housing portion, the lower face of the flange seals against the inner surface of the wall of the bioprocessing container and the upper face of the locking ring contacts the outer surface of the wall of the bioprocessing container when the internal surface of the locking ring is threadably engaged with the external surface of the lower housing portion of the seal housing assembly.

2. The mechanically driven agitator of claim 1, further comprising seal integrity testing assembly, the assembly comprising an inner channel in the seal housing assembly along the rotatable shaft communicating with the upper and lower seal assemblies, wherein the lower housing portion further comprises a port communicating with the inner channel.

3. The mechanically driven agitator of claim 1, wherein the upper and lower seal assembly each further comprise at least one resilient ring that compresses when the seal assembly is fitted into the respective housing portion.

4. The mechanically driven agitator of claim 1, further comprising a coupling fitting attached to the second end of the shaft.

5. The mechanically driven agitator of claim 4, further comprising a coupler device engageable with the coupling fitting.

6. A mixing assembly, comprising
(a) a bioprocessing container comprising a closed container having an interior volume suitable for containing fluid, the container comprising at least one side wall, a top wall, and a bottom wall, the side wall(s) being joined to the top wall and the bottom wall; and at least an inlet port, and a drain port, wherein the bioprocessing container further comprises:
(b) the mechanically driven agitator of claim 1, attached to the bottom wall or the top wall.

7. A tote for supporting a mixing assembly, the tote comprising a floor for receiving the mixing assembly, the floor including an opening for receiving a lower housing portion of a seal housing assembly of the mixing assembly, the mixing assembly comprising
(a) a bioprocessing container comprising a closed container having an interior volume suitable for containing fluid, the container comprising at least one side wall, a top wall, and a bottom wall, the side wall(s) being joined to the top wall and the bottom wall; and at least an inlet port, and a drain port, wherein the bioprocessing container further comprises:
(b) a mechanically driven agitator for use in bioprocessing comprising
a rotatable shaft comprising a cylindrical element having a first end and a second end, the shaft having a vertical rotational axis;
an impeller comprising a hub mounted on the first end of the rotatable shaft, the hub having a horizontal axis perpendicular to the vertical rotational axis of the shaft, and at least two arms extending from the hub;
the seal housing assembly comprising an upper housing portion, and the lower housing portion;
wherein the upper housing portion comprises a shoulder having a shoulder surface and a lower part having an external surface, an upper seal assembly, the upper seal assembly comprising an upper shaft seal and an upper shaft bearing, the upper shaft seal including an upper seal annular opening and the upper shaft bearing including an upper bearing annular opening for receiving the rotatable shaft, wherein the upper shaft bearing is fit onto the shaft; and,
wherein the lower housing portion comprises a lower seal assembly, the seal assembly comprising lower shaft seal and a lower shaft bearing, the lower shaft seal including a lower seal annular opening and the lower shaft bearing including a lower bearing annular opening for receiving the rotatable shaft, wherein the lower shaft bearing is fit onto the shaft, and the second end of the shaft passes through the lower housing portion; the lower housing portion comprising an external surface including threads,
an upper carrier housing located in the upper housing portion, a lower carrier housing located in the lower housing portion, the upper carrier housing comprising the upper shaft seal and the upper shaft bearing, the lower carrier housing comprising the lower shaft seal and the lower shaft bearing, wherein the upper seal assembly and the lower seal assembly each further comprise an anti rotation device, each of the upper and lower carrier housings comprising a carrier housing protrusion formed into each of the upper and lower carrier housings, the anti rotation device comprising a notch in the shaft seal, and the carrier housing protrusion, wherein the protrusion engages with the shaft seal and prevents rotation of the shaft seal;
a locking ring, wherein the locking ring comprises an upper locking ring face and a lower locking ring face and an opening passing through the upper locking ring face and the lower locking ring face, the opening having a surface including threads, wherein the locking ring is threadably engageable with the lower housing portion of the seal housing assembly, and the upper face is suitable for contacting an outer surface of a wall of a bioprocessing container;
a support flange including a flange annular opening for receiving the rotatable shaft, the flange having a flange upper face, and a flange lower face suitable for sealing against an inner surface of the wall of a bioprocessing container; wherein the flange annular opening includes a wall sealably coupled to the external surface of the lower part of the upper housing portion of the seal housing assembly;

wherein the upper face of the flange presses against the surface of the shoulder of the upper housing portion, the lower face of the flange seals against the inner surface of the wall of the bioprocessing container and the upper face of the locking ring contacts the outer surface of the wall of the bioprocessing container when the internal surface of the locking ring is threadably engaged with the external surface of the lower housing portion of the seal housing assembly, the mechanically driven agitator being attached to the bottom wall or the top wall of the bioprocessing container;

the tote further comprising a support assembly comprising:
(i) a moveable seat arranged in the opening in the floor;
(ii) an engagement assembly comprising at least one protrusion for engaging with the lower housing portion of the seal housing assembly; and,
(iii) an actuator for moving the moveable seat to provide a lock between the lower housing portion of the seal housing assembly and the tote after the engagement assembly engages with the lower housing portion of the seal housing assembly, and for unlocking the lower housing portion of the seal housing from the tote.

8. The tote of claim 7, wherein an alignment device is attached to the lower housing portion of the seal housing assembly, and the engagement assembly engages with the alignment device.

9. The tote of claim 7, wherein the support assembly further comprises a first sensor for detecting when the engagement assembly engages with the lower housing portion of the seal housing assembly.

10. The tote of claim 9, wherein the tote further comprises a second sensor for detecting when the actuator has moved the moveable seat to provide the lock.

11. A system comprising the tote of claim 10, further comprising at least first and second indicators receiving signals from the first and second sensors, respectively, wherein the indicators are illuminated when the signals are received.

12. A method for determining seal integrity of a mechanically driven agitator, the method comprising applying pressure to the agitator of claim 2 through the port communicating with the inner channel, and determining whether the pressure is maintained for a desired period of time.

13. The mechanically driven agitator of claim 2, further comprising a coupling fitting attached to the second end of the shaft.

14. A mixing assembly, comprising
(a) a bioprocessing container comprising a closed container having an interior volume suitable for containing fluid, the container comprising at least one side wall, a top wall, and a bottom wall, the side wall(s) being joined to the top wall and the bottom wall; and at least an inlet port, and a drain port, wherein the bioprocessing container further comprises:
(b) the mechanically driven agitator of claim 2, attached to the bottom wall or the top wall.

15. A mixing assembly, comprising
(a) a bioprocessing container comprising a closed container having an interior volume suitable for containing fluid, the container comprising at least one side wall, a top wall, and a bottom wall, the side wall(s) being joined to the top wall and the bottom wall; and at least an inlet port, and a drain port, wherein the bioprocessing container further comprises:
(b) the mechanically driven agitator of claim 4, attached to the bottom wall or the top wall.

16. The tote of claim 8, wherein the support assembly further comprises a first sensor for detecting when the engagement assembly engages with the lower housing portion of the seal housing assembly.

17. The mechanically driven agitator of claim 1, further comprising an upper cap threaded into the upper housing portion to retain the upper seal assembly in the upper housing portion and a lower cap threaded into the lower housing portion to retain the lower seal assembly in the lower housing portion.

* * * * *